United States Patent
Burlot et al.

(10) Patent No.: US 10,940,232 B2
(45) Date of Patent: Mar. 9, 2021

(54) ADHESIVE COMPOSITION AND ELEMENT FOR ATTACHING TO HUMAN SKIN

(71) Applicant: B. BRAUN MEDICAL, Boulogne Billancourt (FR)

(72) Inventors: Delphine Burlot, Anglet (FR); Paul Lassalle, Anglet (FR); Laurent Lalet, Anglet (FR)

(73) Assignee: B. BRAUN MEDICAL, Billancourt (FR)

( * ) Notice: Subject to any disclaimer, the term of this patent is extended or adjusted under 35 U.S.C. 154(b) by 126 days.

(21) Appl. No.: 15/884,981

(22) Filed: Jan. 31, 2018

(65) Prior Publication Data
US 2018/0221534 A1    Aug. 9, 2018

(30) Foreign Application Priority Data

Feb. 3, 2017   (FR) ..................................... 17 50958

(51) Int. Cl.
| | |
|---|---|
| *C09J 145/00* | (2006.01) |
| *A61L 24/06* | (2006.01) |
| *C09J 153/02* | (2006.01) |
| *A61L 24/00* | (2006.01) |
| *A61L 24/04* | (2006.01) |
| *C09J 123/08* | (2006.01) |
| *C09J 153/00* | (2006.01) |

(52) U.S. Cl.
CPC ........... *A61L 24/06* (2013.01); *A61L 24/0031* (2013.01); *A61L 24/0094* (2013.01); *A61L 24/043* (2013.01); *C09J 123/0853* (2013.01); *C09J 153/005* (2013.01); *C09J 153/02* (2013.01); *C08L 2203/02* (2013.01); *C08L 2203/16* (2013.01)

(58) Field of Classification Search
CPC .................. C09J 153/02; C09J 153/005; C09J 123/0853; C09J 11/08; C09J 101/286; C09J 145/00; C09J 189/00; C08L 2203/02; C08L 2203/16; C08L 2205/02; C08L 2205/025; C08L 2205/035; C08L 23/22; C08L 45/00; C08L 53/02; C08L 23/0853; A61L 24/06; A61L 24/0031; A61L 24/0094; A61L 24/043; A61L 15/585
USPC ......................................................... 523/118
See application file for complete search history.

(56) References Cited

U.S. PATENT DOCUMENTS

| | | | |
|---|---|---|---|
| 4,551,490 A * | 11/1985 | Doyle ................... | A61L 15/585 524/22 |
| 4,855,335 A | 8/1989 | Neperud | |
| 6,375,977 B1 | 4/2002 | Auguste et al. | |
| 8,871,993 B2 * | 10/2014 | Buus ...................... | A61L 15/585 602/54 |
| 2009/0076186 A1 * | 3/2009 | Lassalle ................ | A61L 15/585 523/111 |

FOREIGN PATENT DOCUMENTS

| | | |
|---|---|---|
| WO | WO 99/45977 A1 | 9/1999 |
| WO | WO 2011/157278 A1 | 12/2011 |

* cited by examiner

*Primary Examiner* — Hannah J Pak
(74) *Attorney, Agent, or Firm* — Birch, Stewart, Kolasch & Birch, LLP

(57) ABSTRACT

An adhesive composition is intended to provide the attaching to human skin, comprising a continuous phase and a discontinuous phase of hydrocolloids, with the continuous phase comprising by weight, based on the total weight of the adhesive composition: (i) 1 to 12% by weight of a sequenced polymer of the styrene-isoprene-styrene or styrene-butadiene-styrene type, (ii) (a) 1 to 15% of a polymer of the elastomer butyl type, possibly as a mixture with up to 25% by weight of a polymer of the polyisobutylene type, or (b) more than 10% to 30% of a polymer of the polyisobutylene type, free of polymer of the elastomer butyl type, (iii) 1 to less than 10% of a polymer of the ethylene vinyl acetate type, with the sum of these three types of polymers representing from 10 to 40%.

21 Claims, No Drawings

ADHESIVE COMPOSITION AND ELEMENT FOR ATTACHING TO HUMAN SKIN

FIELD OF THE INVENTION

The invention relates to an adhesive composition intended primarily to constitute an adhesive element for example for bags for collecting body fluids, such as ostomy bags or similar elements such as plasters.

TECHNICAL BACKGROUND

Adhesive compositions are known, in particular for bags for collecting body fluids, which comprise a "continuous phase" based on polymers, elastomers, etc. and a "discontinuous phase" containing substantially hydrocolloids.

The continuous phase contains different copolymers, polymers, elastomers which have a texture creating function, optionally plasticizers which have a function for increasing the flexibility of the composition, and tackifier resins.

This terminology, which distinguishes the texture ingredients (elastomers, polymers, copolymers) from plasticizers and tackifier agents or tackifier resins is to be considered in the field considered and is not necessarily absolute. Indeed, most polymers, copolymers and elastomers more or less have texture properties (unless they are liquid or oily), plasticizer and tackifier agent for example in the presence of other ingredients, or certain tackifier resins can also have plasticizer functions. The action of these ingredients must therefore be considered in the framework of adhesive compositions used for the attaching, direct or indirect, of bags for collecting body fluids. However, this terminology makes it possible to distinguish the various adhesive compositions used to attach bags for collecting body fluids.

The adhesive compositions for bags for collecting body fluids are used for the attaching of a bag by direct gluing to the skin of a human being, around an orifice for the removal of excrements. The gluing can be provided to last a relatively short time, which can be less than one day, or a relatively substantial amount of time, which can be about a week. The adhesive compositions used for these various applications therefore have different properties, according to which they must remain fixed for a more or less long length of time. However, they all have a certain number of common properties.

The adhesive compositions for attaching bags for collecting body fluids must first of all have certain mechanical properties. These mechanical properties are substantially firstly the mechanical resistance of a bag, which can have a certain weight, without detachment of the adhesive composition from the skin, then the absence of a leak at the level of the adhesive composition, and finally a good adaptability intended to give good comfort which is not only a good commodity for setting in place and removing, but especially a flexibility that is sufficient so that the patient forgets as much as possible the presence of the adhesive composition and of the bag.

The adhesive compositions for the attaching of bags for collecting body fluids must then have certain chemical properties. It is necessary substantially that the adhesive composition does not provoke irritation of the skin.

Such bags have been known for many years. Typically these bags contain as polymers of polymers of the SIS or SBS type, optionally in a mixture with polymers of the PIB or butyl elastomer type. However, such associations of polymers are not perfect. In particular, if the addition of PIB is beneficial it leads to a certain de-cohesion. It is therefore desirable to have a formulation of polymers that allows for the obtaining of a composition which has a substantial "tack" in order to be able to be put quickly on the skin, adhere strongly by conforming to the abdominal relief in order to support the weight and the constraints of a bag, and enough cohesion to be removed without difficulties and without residue.

Document U.S. Pat. No. 4,855,335 describes a composition comprising 12% to 20% of mineral oil, 30% to 40% of a tackifier resin, 15% to 30% of a hydrocolloid, 5% to 10% of one or several polyisobutylenes, 7% to 15% of a styrene copolymer, and 1% to 8% of an ethylene vinyl acetate copolymer. It is indicated that EVA increases the dimensional stability.

However this formulation is not satisfactory, the quantities in particular of resin and/or hydrocolloid not being suitable for the current compositions.

Document WO2011/157278 describes adhesive compositions comprising 10-50% of a polar phase, with this polar phase comprising an EVA and a polar oil, 10-50% of an apolar phase, this apolar phase comprising a styrene block polymer, and a polyisobutylene or a butyl elastomer, and up to 60% of a hydrocolloid.

However this formulation is not satisfactory, the presence of a polar phase and in particular of a polar oil imposing constraints in terms of components of the composition.

The invention therefore makes it possible to obtain the compromise sought without the constraints of prior art.

SUMMARY OF THE INVENTION

The invention has for object an adhesive composition intended to ensure the attaching on human skin, comprising a continuous phase and a discontinuous phase of hydrocolloids, the continuous phase comprising by weight, based on the total weight of the adhesive composition:

(i) 1 to 12% by weight of a sequenced polymer of the styrene-isoprene-styrene or styrene-butadiene-styrene type, (ii) (a) 1 to 15% of a polymer of the butyl elastomer type, optionally in a mixture with up to 25% by weight of a polymer of the polyisobutylene type, or (b) more than 10% to 30% of a polymer of the polyisobutylene type, free of polymer of the butyl elastomer type, (iii) 1 to less than 10% of a polymer of the ethylene vinyl acetate type, with the sum of these three types of polymers representing from 10 to 40%.

According to an embodiment, the composition is substantially free of polar oil and/or wherein the polar phase represents less than 10% by weight.

According to another embodiment, the continuous phase comprises:

(i) 2 to 8% by weight of a sequenced polymer of the styrene-isoprene-styrene or styrene-butadiene-styrene type, (ii) (a) 2 to 10% of a polymer of the butyl elastomer type, optionally in a mixture with up to 25% by weight of a polymer of the polyisobutylene type, (iii) 2 to less than 10% of an ethylene vinyl acetate polymer.

According to another embodiment, the continuous phase comprises:

(ii) (a) 2 to 10% of a polymer of the butyl elastomer type, free of polymer of the polyisobutylene type.

According to another embodiment, the continuous phase comprises:

(ii) (a) 2 to 10% of a polymer of the butyl elastomer type, as a mixture with from 10 to 25% by weight of a polymer of the polyisobutylene type.

According to another embodiment, the continuous phase comprises:

(i) 2 to 8% by weight of a sequenced polymer of the styrene-isoprene-styrene or styrene-butadiene-styrene type, (ii) (b) from 15% to 30% of a polymer of the polyisobutylene type, free of polymer of the butyl elastomer type, (iii) 2 to less than 10% of an ethylene vinyl acetate polymer.

According to another embodiment, the ethylene vinyl acetate polymer comprises from 30 to 70% by weight of the vinyl acetate monomer.

According to another embodiment, the composition comprises 10 to 30% of tackifier resin. According to another embodiment, the composition comprises 40 to 60% of a discontinuous phase of hydrocolloids.

According to another embodiment, the discontinuous phase comprises a majority of at least one compound chosen from cellulose fibres, carboxymethylcellulose, sodium, cross-linked or other, and hydroxyethylcellulose, as well as compounds similar to gum such as guar or karaya gum or gum arabic, and substances such as xanthans, starches for example potato starch, alginates, pectin, gelatine, psyllium, carob extract, agarose, carrageenans, polyacrylamides, or mixtures thereof.

According to another embodiment, the discontinuous phase is free from products of animal origin.

The invention also has for object an element for the attaching of a bag for collecting body fluids, comprising the adhesive composition according to the invention and, on the face opposite that which is intended to be in contact with the skin, a film.

According to another embodiment, the film is a polyethylene film or ethylene-vinyl acetate copolymer or the mixture thereof, more preferably with a thickness of 25 to 100 µm.

The invention therefore provides an adhesive composition, namely a composition which is adhesive with pressure.

The use of the three compounds, SIS or SBS, EVA and butyl elastomer and/or PIB in the polymer mass according to the proportions indicated makes it possible to obtain the compromise and the three additional behaviours. The styrene copolymer (SIS or SBS) makes it possible to obtain an adhesive with substantial immediate tack, a cohesion and a structure in the adhesive composition. The EVA makes it possible to decrease the elasticity of the network by making it more plastic. The polyisobutylene (PIB) or Butyl makes it possible to take over from the resins by giving a stronger adhesiveness, in particular with low molecular weights by increasing the conformability of the adhesive composition.

In this application, all of the % are given by weight in relation to the total weight of the adhesive composition.

DESCRIPTION OF EMBODIMENTS OF THE INVENTION

Polymers of the SIS or SBS type

These polymers are conventional and known in the art. These are block copolymers based on styrene and isoprene or butadiene (or a mixture of the two).

The texture copolymer of the continuous phase of the styrene-isoprene-styrene or styrene-butadiene-styrene type, is constituted preferably of a styrene-isoprene-styrene sequenced copolymer. These polymers can contain variable quantities of diblocks or triblocks, with double or triple sequences.

Reference can be made for a description of these polymers to document WO2011/157278, page 8, lines 6-18, passage to which it is expressly referred to. Reference can also be made to document U.S. Pat. No. 4,855,335, col. 3, lines 16-23 passage to which it is expressly referred to.

Examples of copolymers of the styrene-isoprene-styrene or styrene-butadiene-styrene texture type that are suitable according to the invention are for example certain copolymers "Kraton" from Shell Chemical Company, for example of the D11 type (D1161, D1117 and D1112), or these copolymers such as "Vector 4113" from Dexco or "Cariflex S-1707" from Shell.

Polymers of the Butyl or PIB Type

These polymers are also conventional.

The polymer conventionally identified under the term "butyl" is a polybutyl elastomer comprising a minority portion of isoprene. Use can be made of those commercialised under the names Butyl 268 from Exxon, or Butyl BK from Togliatti/Nizhnekamsk.

The molecular weight of the butyl elastomer is adapted to the application, for example a molecular weight Mn from 200,000 to 600,000.

The polymer PIB is also well known to those skilled in the art. Those of the Oppanol range available from BASF can be used, with for example grades B10, B12 and B15. The molecular weight of the PIB is adapted to the application, for example a molecular weight Mn less than 100,000, preferably from 40,000 to 60,000.

EVA

This type of polymer is also known. Those comprising from 30 to 70% by weight of monomer vinyl acetate can for example be used.

Those of the LEVAMELT range of grades 400 or 700 or of the Evatane range can be used.

Tackifier Resins

The tackifier resins used in the invention are conventional.

More precisely, tackifier resins, the tackifier agent used can include a mixture of high-activity tackifier resins, for example based on terpene resins, and/or having medium activity, and/or having low activity but furthermore having reinforcing properties. Reference can be made to document EP1871845 for a description of the suitable tests.

These tackifier resins are conventional. Resins of the terpene type can thus be used, for example terpene-styrene, that can have a softening temperature of about 105° C. (ring and ball method) and a molecular weight by mass of about 1000. Resins that also have a reinforcing action can also be used. For example a thermoplastic polymer derived substantially from α-methylstyrene having for example a molecular weight by mass between 300 and 3000 can be used. The elasticity of the composition can thus be modulated. Totally hydrogenated resins can also be used.

Examples of such resins are the resins commercially available under the names Regalite, Arkon, Dercolyte, Piccolyte S, Zonatac, Kristalex, Piccotex and Escorez.

The respective quantities of the various types of resins can vary such as will be appreciated by those skilled in the art.

Hydrocolloid

The discontinuous phase constituted of hydrophilic polymers in the form of hydrocolloids is of the type well known in the art, containing a substantial quantity of compounds such as cellulose fibres, carboxymethylcellulose, sodium, cross-linked or other, and hydroxyethylcellulose, as well as compounds similar to guar gum, and substances such as xanthans, alginates, pectin, gelatine, psyllium, carob extract, gum arabic, agarose, carrageenans and polyacrylamides.

The hydrocolloids used in the invention are conventional.
Plasticizer

A plasticizer will be used, which more preferably is an apolar oil. An example of such an oil or plasticizer is a polyalphaolefin, such as the one available under the name Durasyn. A mineral oil, a paraffin, a castor oil, a synthetic paraffin wax from Shell, the "Sun 5512" resin from Sun or "Primol" from Hercules can also be used.

The adhesive composition can comprise other agents or additives, such as an agent with medicinal action, for example chosen from chitosan and α-L-fucose, or additives such as antioxidants.

The invention also relates to an element for attaching a bag for collecting body fluids comprising the aforementioned adhesive composition and, on the face opposite the one that must be in contact with the skin, a conventional coating film known in the art.

Such a film is a polyethylene or EVA film, of suitable thickness.

Examples of Composition

The compositions of the table are prepared by mixing constituents, according to the proportions by weight. The components are given in the table. The order of introduction is that which appears in the table.

After each introduction, a mixing of about 10 min is implemented in order to obtain good homogeneity. The final mixing lasts about 50 min. The composition thus obtained is extruded, with an extrusion time of about 60 min, in the form of a sheet 1 mm thick and cut into elements used for tests for attaching bags for collecting body fluids.

The elements are then tested.

Fmax and Tack: The test consists in the pulling off of a punch executed using a traction machine and measuring the force required for the pulling off of the punch (Fmax), in determined conditions of contact time with the composition before pulling off and of the pulling off speed. The tack is measured with the same test but with very short contact times.

Fcompression and % relaxation: the test consists of a compression test executed using a traction machine to measure the rigidity (Fcompression) as well as the capacity for relaxation (% relaxation), in determined conditions of contact time with the composition.

The following table gives the compositions and the values of the measurements of the tests.

| | Formulas | 1 | 2 | 3 | 4 | 5 | 6 |
|---|---|---|---|---|---|---|---|
| SIS | Kraton D1161 | 3.04 | | 6.50 | | | 4.56 |
| | Vector 4113 | | 3.04 | | 6.5 | 5.5 | |
| EVA | Levamelt 686 | 3 | 3 | 2.6 | 2.6 | 6.5 | 3 |
| | Levamelt 400/EVATAN 40/55 | | | 2.1 | 2.1 | 3 | 2 |
| Butyl | Butyl 268 | 7.44 | 7.44 | 7.27 | 7.27 | 3 | 3 |
| PIB | Oppanol B15 | | | | | 13 | 12 |
| | Oppanol B12 | 11.00 | 11 | | | | 6 |
| | Oppanol B10 | 9 | 9 | | | | |
| Resins | Régalite | 9.02 | | | | 3.3 | |
| | Dercolyte | | | 15.43 | | | |
| | Piccolyte S | | 5.3 | | 13.33 | 7.3 | 7.7 |
| | Kristalex | | 3.46 | 6.5 | | | |
| | Piccotex | 3.46 | | | 6.5 | 5.5 | 5.19 |
| | Escorez | | 3.72 | | | | |
| Plasticizer | Durasyn | 5.04 | 5.04 | 11.6 | 13.7 | 9.9 | 7.55 |
| Hydrocolloids | CMC7M | 12.00 | 8 | 11 | | | |
| | Guar | 10.00 | 9 | 9 | 12 | 7 | 11 |
| | CMC12M | | 7 | | 14 | 15 | 14 |
| | Gelatine | 16.00 | 14 | 12 | 11 | | 15 |
| | Pectin | 11.00 | 11 | 11 | 11 | 12 | 9 |
| | Superabsorbant A500 | | | 5 | | 8.5 | |
| Characteristics | Tack | 1.15 | 1.15 | 1.27 | 1.25 | 1.35 | 1.20 |
| | Fmax | 4.60 | 4.80 | 3.20 | 3.40 | 3.80 | 3.00 |
| | F compression | 3.10 | 3.00 | 2.50 | 2.40 | 2.60 | 2.50 |
| | % relaxation | 67.00 | 65.00 | 60.00 | 60.00 | 72.00 | 65.00 |

Consideration is now given to other properties of the compositions according to the invention.

Tests in Patients

Tests have been conducted in the conditions of a hospital environment, i.e. wherein the installation and the removing are carried out by hospital personnel. The hospital personnel or the patients determined several parameters among which the immediate adhesiveness, the presence of residue on the skin after the removal of the composition, the facility in applying the bag, the facility in removing the bag, the conformability and the adhesiveness of the bag when it is worn by the patient.

The results obtained are excellent and the compromise is reached.

As such, the invention relates to adhesive compositions and elements for attaching that have the compromise sought for ostomy bags.

The invention claimed is:

1. An adhesive composition intended to provide the attaching on human skin, comprising a continuous phase and a discontinuous phase of hydrocolloids, the continuous phase comprising by weight, based on the total weight of the adhesive composition:
   (i) 1 to 12% by weight of a sequenced polymer of styrene-isoprene-styrene or styrene-butadiene-styrene,
   (ii) (a) 1 to 15% by weight of a butyl elastomer polymer, optionally in a mixture with up to 25% by weight of a polyisobutylene polymer, or (b) from 15% to 30% by weight of a polyisobutylene polymer, free of butyl elastomer polymer,
(iii) 1 to less than 10% by weight of an ethylene vinyl acetate polymer,
with the sum of these three types of polymers representing from 10 to 40% by weight,
and wherein the composition comprises 40 to 60% by weight of discontinuous phase of hydrocolloids.

2. The composition according to claim 1, wherein the composition is free of polar oil and/or wherein polar phase represents less than 10% by weight.

3. The composition according to claim 1, wherein the continuous phase comprises:
(i) 2 to 8% by weight of the sequenced polymer of styrene-isoprene-styrene or styrene-butadiene-styrene,
(ii) (a) 2 to 10% by weight of the butyl elastomer polymer, optionally in a mixture with up to 25% by weight of the polyisobutylene polymer,
(iii) 2 to less than 10% by weight of the ethylene vinyl acetate polymer.

4. The composition according to claim 1, wherein:
(ii) (a) 2 to 10% by weight of the butyl elastomer polymer, free of polyisobutylene polymer.

5. The composition according to claim 1, wherein:
(ii) (a) 2 to 10% by weight of the butyl elastomer polymer, in a mixture with from 10 to 25% by weight of the polyisobutylene polymer.

6. The composition according to claim 1, wherein the continuous phase comprises:
(i) 2 to 8% by weight of the sequenced polymer of styrene-isoprene-styrene or styrene-butadiene-styrene,
(ii) (b) from 15% to 30% by weight of the polyisobutylene polymer, free of butyl elastomer polymer,
(iii) 2 to less than 10% by weight of the ethylene vinyl acetate polymer.

7. The composition according to claim 1, wherein the ethylene vinyl acetate polymer comprises from 30 to 70% by weight of vinyl acetate monomer.

8. The composition according to claim 1, wherein the composition further comprises 10 to 30% by weight of tackifier resin.

9. The composition according to claim 1, wherein the discontinuous phase comprises a majority of at least one compound chosen from cellulose fibers, crosslinked or non-crosslinked carboxymethylcellulose, sodium, hydroxyethylcellulose, guar or karaya gum or gum arabic, xanthans, starches, alginates, pectin, gelatine, psyllium, carob extract, agarose, carrageenans, polyacrylamides, or mixtures thereof.

10. The composition according to claim 1, wherein the discontinuous phase is free from products of animal origin.

11. An element for attaching a bag for collecting body fluids, comprising the adhesive composition as claimed in claim 1 and, on the face opposite that which is intended to be in contact with the skin, a film.

12. The element according to claim 11, wherein the film is a polyethylene film or ethylene-vinyl acetate copolymer or the mixture thereof.

13. The composition according to claim 2, wherein the continuous phase comprises:
(i) 2 to 8% by weight of the sequenced polymer of styrene-isoprene-styrene or styrene-butadiene-styrene,
(ii) (a) 2 to 10% by weight of the butyl elastomer polymer, optionally in a mixture with up to 25% by weight of the polyisobutylene polymer,
(iii) 2 to less than 10% by weight of the ethylene vinyl acetate polymer.

14. The composition according to claim 2, wherein:
(ii) (a) 2 to 10% by weight of the butyl elastomer polymer, free of polyisobutylene polymer.

15. The composition according to claim 3, wherein:
(ii) (a) 2 to 10% by weight of the butyl elastomer polymer, free of polyisobutylene polymer.

16. The composition according to claim 2, wherein:
(ii) (a) 2 to 10% by weight of the butyl elastomer polymer, in a mixture with from 10 to 25% by weight of the polyisobutylene polymer.

17. The composition according to claim 3, wherein:
(ii) (a) 2 to 10% by weight of the butyl elastomer polymer, in a mixture with from 10 to 25% by weight of the polyisobutylene polymer.

18. The composition according to claim 2, wherein the continuous phase comprises:
(i) 2 to 8% by weight of the sequenced polymer of styrene-isoprene-styrene or styrene-butadiene-styrene,
(ii) (b) from 15% to 30% by weight of the polyisobutylene polymer, free of butyl elastomer polymer,
(iii) 2 to less than 10% by weight of the ethylene vinyl acetate polymer.

19. The composition according to claim 2, wherein the ethylene vinyl acetate polymer comprises from 30 to 70% by weight of vinyl acetate monomer.

20. An adhesive composition intended to provide the attaching on human skin, comprising a continuous phase and a discontinuous phase of hydrocolloids, the continuous phase comprising by weight, based on the total weight of the adhesive composition:
(i) 1 to 12% by weight of a sequenced polymer of styrene-isoprene-styrene or styrene-butadiene-styrene,
(ii) (a) 1 to 15% by weight of a butyl elastomer polymer, optionally in a mixture with up to 25% by weight of a polyisobutylene polymer, or
(iii) 1 to less than 10% by weight of an ethylene vinyl acetate polymer,
with the sum of these three types of polymers representing from 10 to 40% by weight,
and wherein the composition comprises 40 to 60% by weight of discontinuous phase of hydrocolloids.

21. The element according to claim 12, wherein the film is with a thickness of 25 to 100 μm.

* * * * *